(12) United States Patent
Wung et al.

(10) Patent No.: US 6,186,011 B1
(45) Date of Patent: Feb. 13, 2001

(54) METHOD OF ANALYZING SPOT WELDED STRUCTURES

(75) Inventors: Pey Min Wung, Troy; William Steven Stewart, Dearborn, both of MI (US)

(73) Assignee: Ford Global Technologies, Inc., Dearborn, MI (US)

( * ) Notice: Under 35 U.S.C. 154(b), the term of this patent shall be extended for 0 days.

(21) Appl. No.: 09/347,558

(22) Filed: Jul. 6, 1999

(51) Int. Cl.$^7$ .................................................... G01N 3/20
(52) U.S. Cl. ............................................................ 73/850
(58) Field of Search .............................. 73/850, 851, 848, 73/856

(56) References Cited

U.S. PATENT DOCUMENTS

| | | | |
|---|---|---|---|
| 3,880,535 | * | 4/1975 | Durham et al. ........................ 403/241 |
| 4,027,529 | * | 6/1977 | Olsen ....................................... 73/827 |
| 5,602,341 | * | 2/1997 | Lee et al. ................................ 73/850 |
| 5,785,463 | * | 7/1998 | Eaton et al. ........................ 405/302.2 |

* cited by examiner

Primary Examiner—Max Noori

(57) ABSTRACT

Method of analyzing spot welded sheet metal structures subjected to forces that promote one or more basic failure modes of either shear tension, in-plane rotation, coach peel, normal tension, or any combination of such basic modes, the method comprising: (i) providing spot welded sheet metal test coupons for analysis of the selected failure mode for the structure to be analyzed and subjecting such test coupons to progressively increasing forces that eventually achieve failure in the selected failure mode to thereby generate measured load and displacement test data; (ii) analyzing the data from the basic modes to derive and extract spot weld strength and stiffness information and then surface fitting such extracted data to create a database; (iii) establishing a computer math model for simulating the spot weld failure modes of the structure and populating the database thereinto to enable simulated physical tests of the structure; (iv) creating a cumulative-damage failure criterion for the spot welded structure that ratios (a) the resultant strength information from the populated math model for selected combinations of load and selected combinations of time and structure thickness, and (b) the measured strength information derived for such combinations of load derived from the test data; and (v) solving the criterion to determine whether it indicates failure for the combination of resultant strength and other values selected.

8 Claims, 7 Drawing Sheets

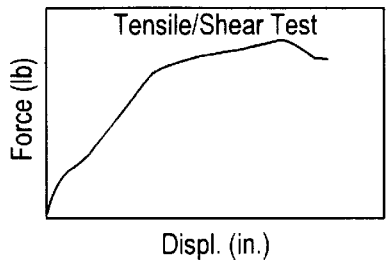

FIG. 12

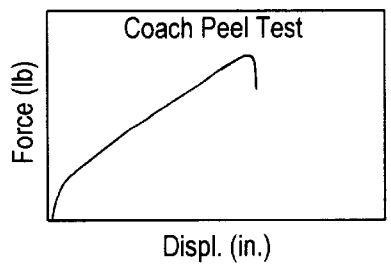

FIG. 13

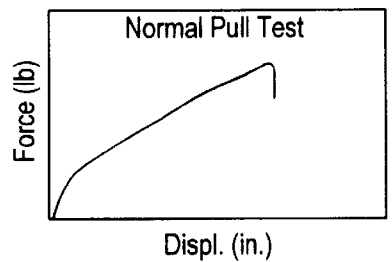

FIG. 14

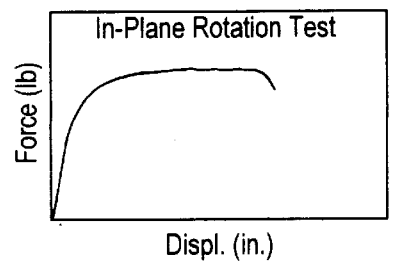

FIG. 15

Tensile/Shear Mode Stiffness/Strength

| sheet 1 Thickness $t_1$ (in) | sheet 2 Thickness $t_2$ (in) | | | | |
|---|---|---|---|---|---|
| | | | | | |
| | | | | | |
| | | | | | |
| | | | | | |

Coach Peel Mode Stiffness/Strength

| sheet 1 Thickness $t_1$ (in) | sheet 2 Thickness $t_2$ (in) | | | | |
|---|---|---|---|---|---|
| | | | | | |
| | | | | | |
| | | | | | |
| | | | | | |

Normal Pull Mode Stiffness/Strength

| sheet 1 Thickness $t_1$ (in) | sheet 2 Thickness $t_2$ (in) | | | | |
|---|---|---|---|---|---|
| | | | | | |
| | | | | | |
| | | | | | |
| | | | | | |

In-Plane Rotation Mode Stiffness/Strength

| sheet 1 Thickness $t_1$ (in) | sheet 2 Thickness $t_2$ (in) | | | | |
|---|---|---|---|---|---|
| | | | | | |
| | | | | | |
| | | | | | |
| | | | | | |

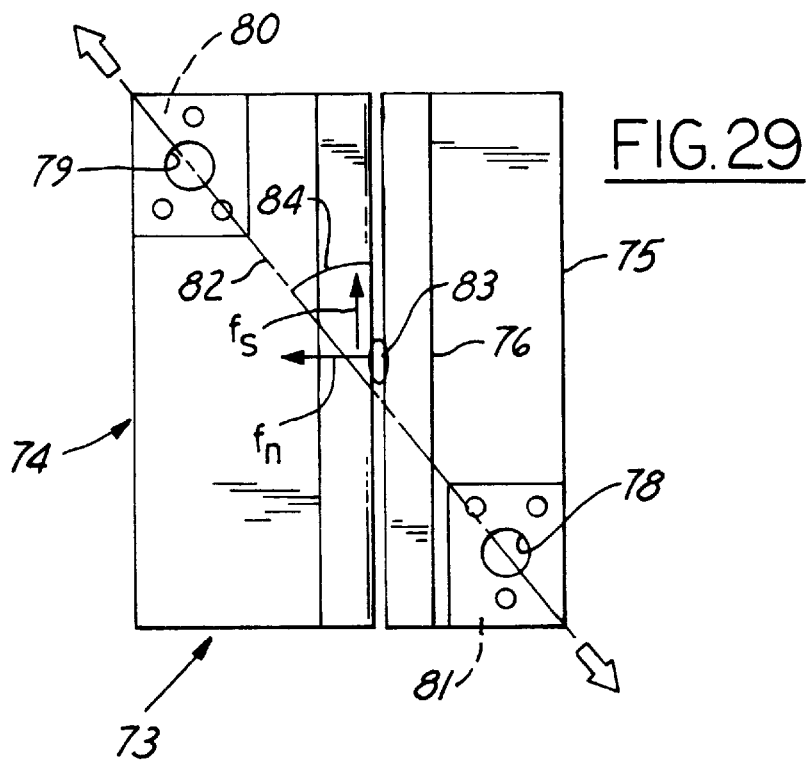
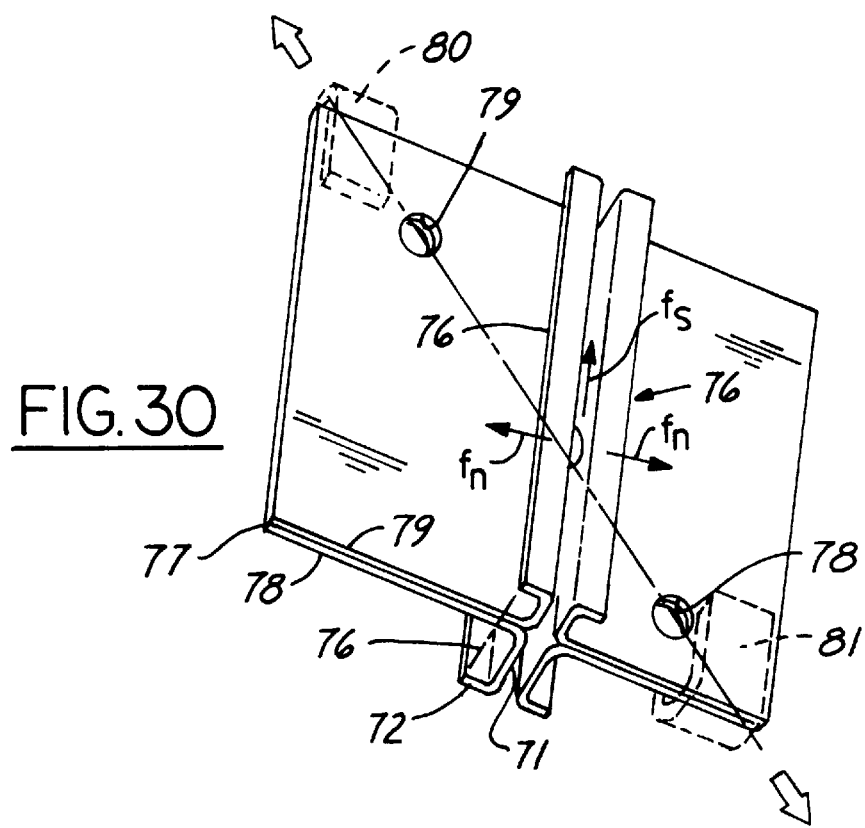

METHOD OF ANALYZING SPOT WELDED STRUCTURES

BACKGROUND OF THE INVENTION

1. Technical Field

This invention relates to procedures for developing a resultant force based spot weld failure criterion for predicting multi-axial loaded spot weld failure.

2. Discussion of Prior Art

Spot welding is widely used in joining sheet metal members in the manufacture of automotive bodies because such welding can be extremely fast. Spot welding is the simplest form of resistance welding in which electrodes apply some pressure when squeezingly contacting the sheet metal assembly while low voltage current, accompanied by sufficient amperage, is passed between the electrodes to locally raise the sheet metal to a melting and welding temperature.

The strength and stiffness of the spot weld joints can vary considerably depending on the direction, complexity and cyclic nature of the joint loading. The unreliability of current methods to predict the failure mode of a specific spot welded joint in automotive bodies has misled designers to inaccurately design spot weld structures out of an abundance of precaution. With the imposition of stricter fuel economy standards for automotive vehicles, the spot weld body structures have come under severe scrutiny to allow for weight reduction.

Existing structural analysis techniques for spot welded structures consider only two types of loadings or failure modes at any one time that may act on a structure; such method lacks the increased accuracy and reliability that will assist in structural safety and weight reduction without jeopardizing risk of failure over the useful life of the structure. Often, different failure modes act on the welded structure at the same time, including a variety of modes selected from shear tension, in-plane rotation, coach-peel, and normal or pull tension. These failure modes need to be considered not only by themselves, but in combination for predicting accurate conditions for combined failure of the spot welded structure.

SUMMARY OF THE INVENTION

What is needed is an improved method technique for analyzing spot welded structures that enhance accuracy of predicting failure modes at specific load type, load cycle, and sheet metal thickness.

It is also an object of this invention to practice the method technique herein with computerized test simulation software to provide a computerized model of spot weld structures into which measured strength and stiffness data is referenced for analyzing any intended design.

It is another object of this invention to practice such method technique by use of novel test metal coupons for unitary of mixed failure modes; such coupons, when tested to failure, should provide increased accuracy for strength and stiffness data needed by the method technique herein.

In a first aspect, the invention meeting the above objects, is a method of analyzing spot welded sheet metal structures subjected to forces that promote one or more basic failure modes of either shear tension, in-plane rotation, coach peel, normal tension, or any combination of such basic modes, the method comprising: (i) providing spot welded sheet metal test coupons for analysis of the selected failure mode for the structure to be analyzed and subjecting such test coupons to progressively increasing forces that eventually achieve failure in the selected failure mode to thereby generate measured load and displacement test data; (ii) analyzing the data from the basic modes to derive and extract spot weld strength and stiffness information and then surface fitting such extracted data to create a database; (iii) establishing a computer math model for simulating the spot weld failure modes of the structure and populating the database thereinto to enable simulated physical tests of the structure; (iv) creating a cumulative-damage failure criterion for the spot welded structure that ratios (a) the resultant strength information from the populated math model for selected combinations of load and selected combinations of time and structure thickness, and (b) the measured strength information for such combinations of load derived from the test data; and (v) solving the criterion to determine whether it indicates failure for the combination of resultant strength and other values selected.

The invention, in a second aspect, is a structural test coupon for measuring characteristics of a spot welded structure when tested to failure in a selected mode, the coupon comprising: first and second parts, each part having a panel mated to the other and structurally joined by spot weld at such mating; each part has an integral force pulling panel which is effective to apply one or more of shear tension, in-plane rotation, coach-peel, or normal tension.

BRIEF DESCRIPTION OF THE DRAWINGS

FIGS. 12–15 are data diagrams for fitting curves and surfaces for the respective basic coupon tests of FIGS. 4–11;

FIGS. 16–19 are corresponding fitting surface database tables for each respective data diagram of FIGS. 12–15 for incorporation into the computer model.

FIGS. 29–30 are, respectively, side elevational and perspective views of a combination coupon for generating normal pull and in-plane shear.

DETAILED DESCRIPTION AND BEST MODE

Figure 1:
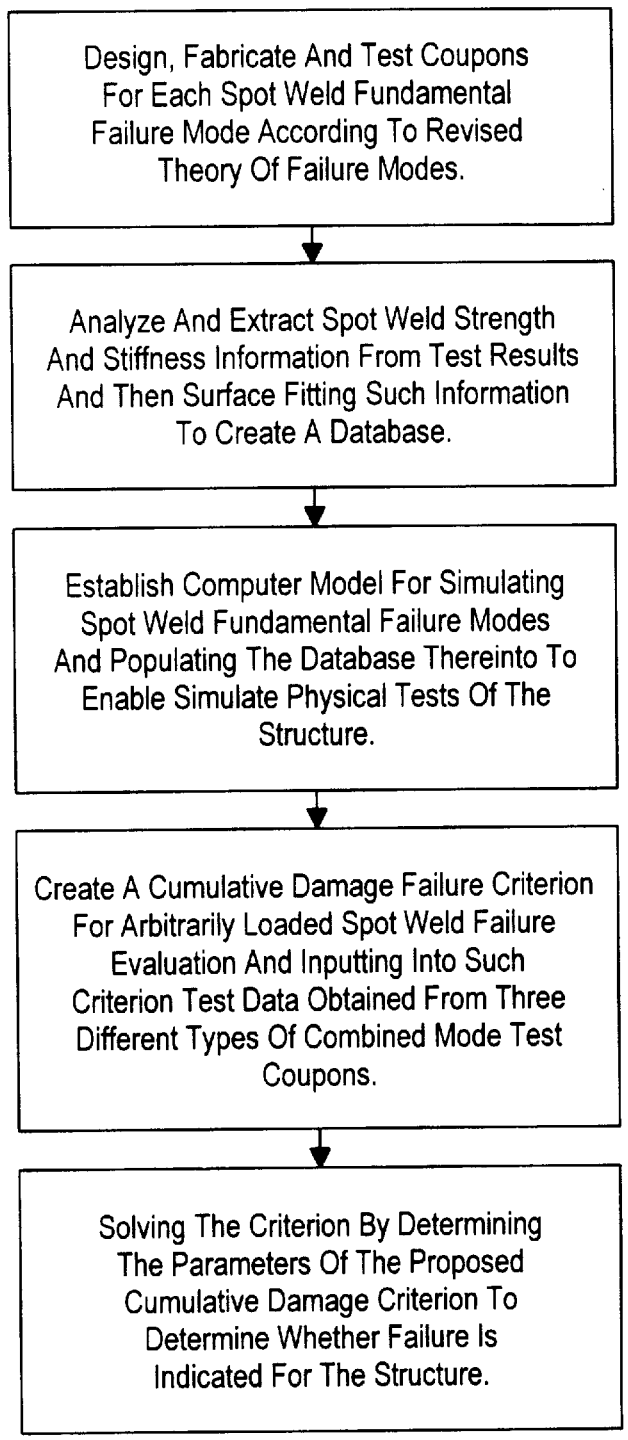
FIG. 1 is a flow diagram of the basic process steps of this invention.

Referring to FIG. 1 (and step 1 thereof), four spot weld basic or fundamental failure modes are identified, which include shear tension, coach peel, normal pull tension and in-plane rotation; test coupons are designed, fabricated and tested for each of these basic modes. In step 2, the measured test results are analyzed so that spot weld strength and stiffness information can be extracted and fitted with math equations for each fundamental failure mode. The math fitting equations create test databases for use with computer math model simulations which are established in step 3. Once good correlations are reached between measured physical tests and computer math model simulations for single spot weld failure modes, step 5 requires a cumulative damage law or criterion to be used for evaluating spot weld failure under any arbitrary combined loading conditions. In step 6, the criterion is solved by use of law parameters that are determined and verified with at least three different combined-mode coupon tests.

Figure 2:
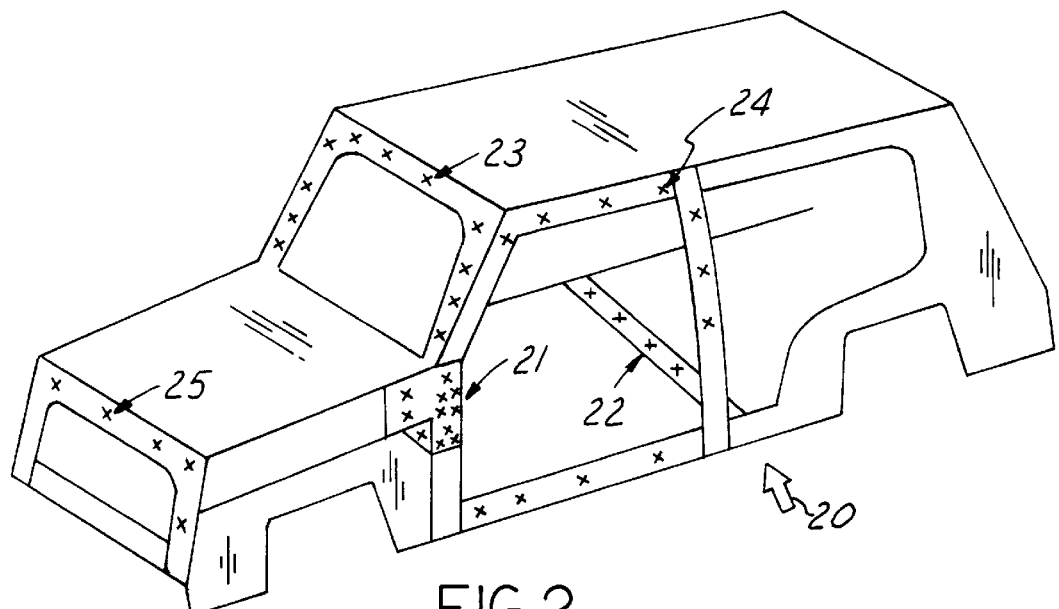
FIG. 2 is a perspective schematic view of an automotive body illustrating the various types of spot welded joints that may be incorporated.
Figure 3:
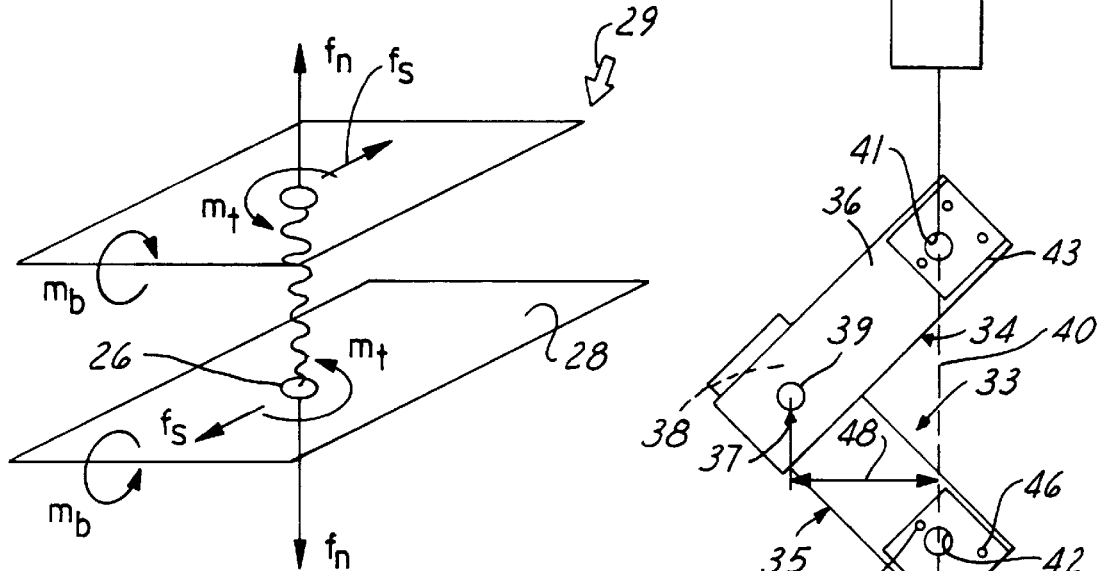
FIG. 3 is a schematic diagram of spot welded joint parameters.

An automotive body structure 20 (as shown in FIG. 2) may have many different types of spot welded joints 21–25, each joint being subjected during vehicle service to different loading conditions. To understand such spot welds, FIG. 3 sequentially depicts a singular spot weld 26 between two sheet metal pieces 27, 28 which can be subjected to a variety of loading modes or forces that comprise: shear $f_s$, normal pull $f_n$, peeling bending moment $m_b$, in-plane torque $m_t$, and any combination of the foregoing. This invention provides a technique for analyzing the design of any such body structure having spot welded joints in order to predict when and how such body structure or joints will fail.

Performing Spot Weld Fundamental Failure Mode Tests

Figure 3A:
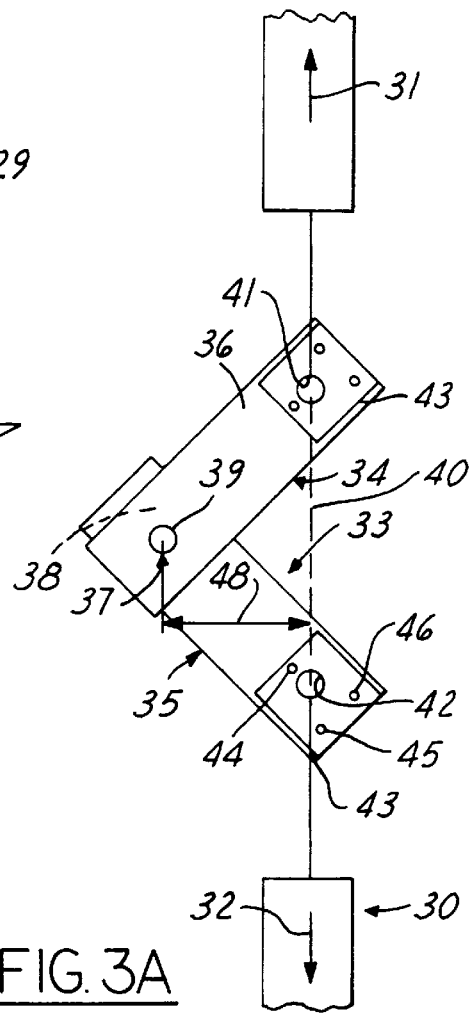
FIG. 3A is a schematic elevational illustration of a test machine showing how a selected test coupon is utilized in carrying out the method.

There must be a generation of load and displacement test data for each type of loading mode applied to different sheet metal thicknesses and compositions. Test coupons 29 for each loading mode are constructed to isolate the effect of the selected loading modes. Each coupon is placed in an unaxial tensile test machine 30 (see FIG. 3A) that applies aligned pulling forces 31, 32 in opposite directions. By designing the test coupons 29 with different configurations, the spot weld of the coupon can be subjected to one or more of the basic failure modes.

Figure 4:
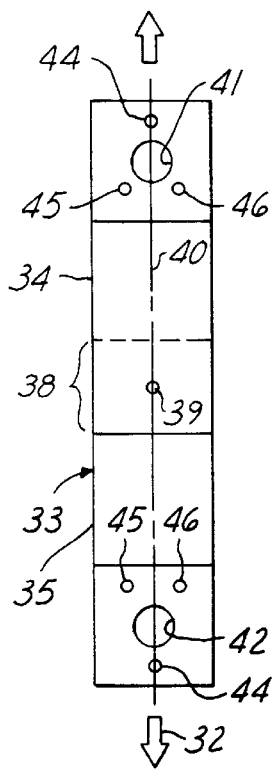
FIGS. 4–11 are various plan or elevational views of different test coupons that are effective with the method of this invention for accurately generating spot weld failure mode test data for respectively shear tension, coach-peel, normal pull tension, and in-plane rotation.
Figure 5:
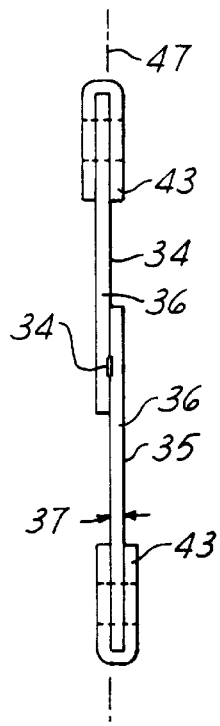

FIGS. 4 and 5 illustrate a test coupon 33 for generating the effect of shear. The coupon 33 has a first part 34 and a second part 35, each being comprised of a strip of sheet metal 36 of the same or different selected test thickness, such as 0.65–0.91 mm.; the strips 36 are overlapped at a region 38 and spot welded at a location 39 on the centerline 40 extending between two pin receiving holes 41, 42 through which machine pulling forces 31, 32 can be applied as indicated by the large arrows. To avoid any distortion due to local sheet metal rupture at the pin receiving openings 41, 42 prior to spot weld failure, another ply of sheet metal 43 is wrapped about the end of the part possessing an opening 41 or 42; the extra ply of sheet metal 43 is spot welded at locations 44, 45, 46 for reinforcement, but which spot welds do not affect the test. Such reinforcing ply ensures that the load and displacement data from the test will be accurate with respect only to the test spot weld at location 39. Upon progressive and increasing pulling forces by the test machine, both a shear force $f_s$ along the plane 47 of the overlapped strips containing the spot weld as well as a torsional in-plane rotational force $f_t$ on the spot weld will take place. The torsional moment is determined by the offset distance 48 from the line 49 of pull.

Figure 6:
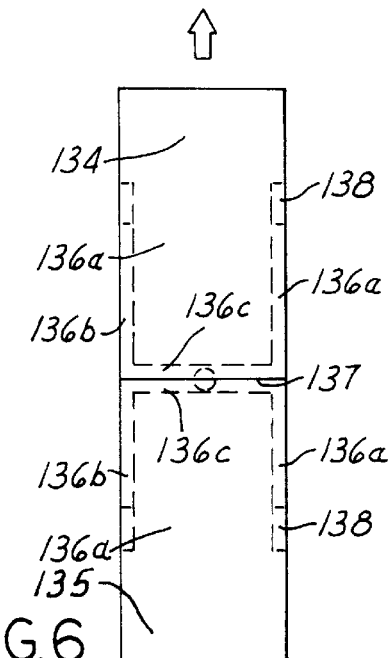
Figure 7:
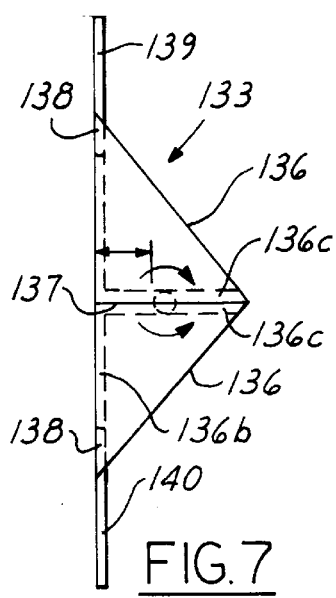

As shown in FIGS. 6 and 7, a test coupon 133 is designed to obtain the load displacement data for a spot weld subjected to bending moment $m_b$ (coach peel). To this end, the first and second parts 134, 135 are each constructed with a right angle wedged shaped box 136 having four sides 136a, 136b, 136c and 136d meeting on a common surface 137 to close the right angle wedge-shaped box with fillet weld 138. Ears 139, 140 extend from each wedged box 136 which is at a right angle 90° to the surface 137. When the machine grips the ears, the opposed pulling forces apply opposed but equal amount bending moment $m_b$ to the spot weld. The magnitude of the bending moment $m_b$ is determined by the product of the applied force and the distance 141 between the edge of the spot weld to the ears 139.

Figure 8:
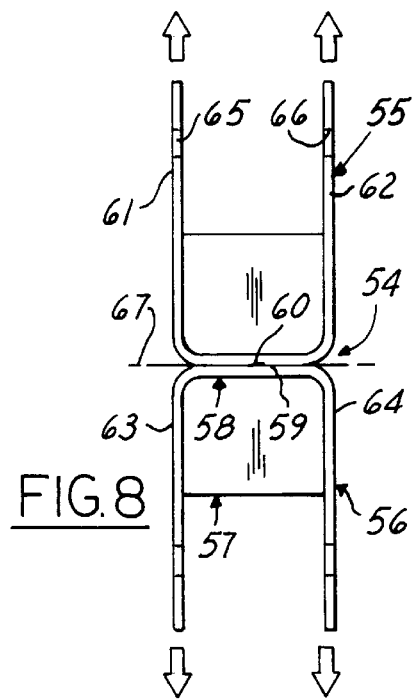
Figure 9:
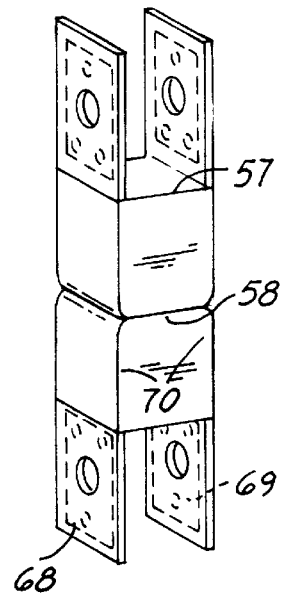

To test for pulling solely in a direction normal to the plane of the spot weld, coupon 54 is used, as shown in FIGS. 8 and 9. First and second sheet metal parts 55, 56 are each shaped from sheet metal of the same or different test thickness to form a four-sided box 57 closed at one end 58 by a panel 59 that is to be spot welded at 60. Ears 61, 62 extend from respective opposite sides 63, 64 of each part's box and have aligned openings 65, 66 in which pins of the test machine 30 can grip for exerting the opposed pulling action that results in pure separating forces on the spot weld that are normal to the plane 67 of the weld at 60. Again, reinforcement ply 68, 69 may be used to avoid any tearing of the ears at the pin openings before failure of the spot weld at 60. It is convenient to form the ears and boxes from a single ply of sheet metal and then fold such ply to obtain the desired shape accompanied by fillet welded side edges 70 of the sheet metal to form and rigidify the box edges.

Figure 11:
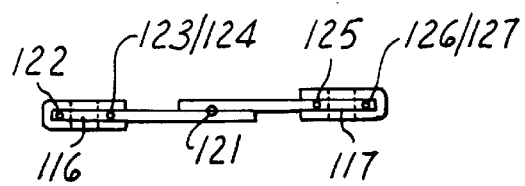
Figure 10:
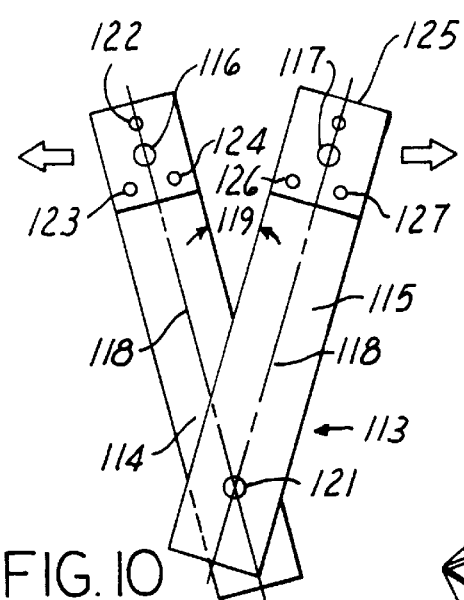
Figure 20:
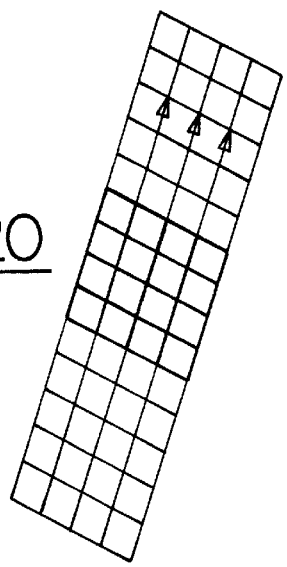
FIGS. 20–23 are math model screen representations for the respective four basic failure mode test coupons.
Figure 21:
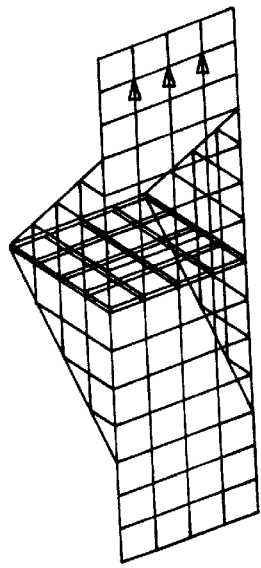
Figure 23:
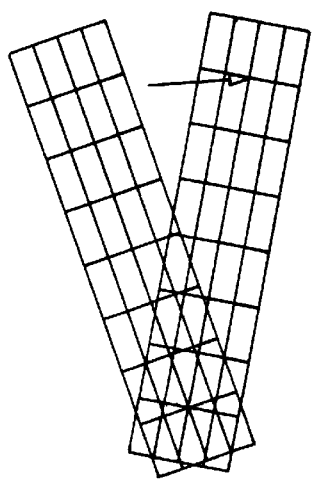
Figure 22:
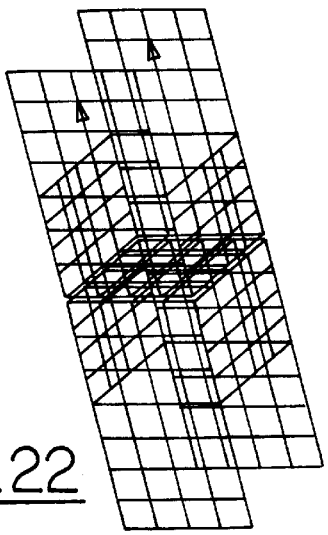

As shown in FIGS. 10–11, a test coupon 113 is designed to obtain load and displacement data for only in-plane rotation (torsion) acting on the spot weld. First and second parts 114, 115 are each formed as a simple strip of sheet metal, each with a pin receiving opening 116, 117 at one end. These pin receiving holes 116, 117 are located on a longitudinal center line 118 for each strip and reinforced with a wrapping of sheet metal 128, 129 which are connected to the metal strip parts 114, 115 by spot welds 122–124 for one and 125–127 for the other. The strips are superimposed at the other end region 120 of each strip and spot welded at a location 121 also on the center line 118 of each strip, with the strip center line of one part 114 being at an angle to the strip center line of the other part 115, such as at an angle 119 of approximately 25°. When opposed forces are applied by the pulling machine along the direction of the large arrows indicated, an in-plane rotational torque (moment) $f_t$ is applied to the spot weld location 121.

Establish Spot Weld Stiffness Databases and Establish Strength Databases

The second step of the process is to derive and extract strength and stiffness data or information from the fundamental failure mode load and displacement test results. The load and displacement data permits one to obtain discrete tensile strength values, as well as stiffness values, from the slope of the curves of the curves plotting force (see FIGS. 12–15). Strength and stiffness will change as a function of varying sheet metal thicknesses for the welded structures. Specific test data points can be tabulated in spreadsheets (as shown in FIGS. 16–19); not all test points will populate the spreadsheets and thus vacant spaces can be derived by interpolation. Surface fitting of the test data to varying thickness combinations is carried out by solid modeling equations such as illustrated at the bottom of each table in FIGS. 16–19. Diagrams (FIGS. 12–15) of the load/displacement data for different failure modes are valuable in that strength and stiffness values can be interpolated between the actual data test points to render continuous curves (such diagrams and tables hereinafter are called test data derived information).

Computer Simulation of Fundamental Failure Modes

The third step is to establish computer models to simulate the spot weld fundamental failure mode tests conducted in the first step. In this part work, the spot weld stiffness and strength databases, set up in the second step, are used to get the best computer simulation. Four different types of mathematical models are built (FIGS. 20, 21, 22 and 23) for the four fundamental failure mode tests correspondingly. Techniques for creating a computer model from a database is known to those skilled in the computer arts.

Resultant Force-Based Sot Weld Failure Criterion

The fourth step is to develop a spot weld failure criterion. In order to ensure the robustness and reliability of this failure criterion, three different types of combined (not fundamental type) failure mode coupons are designed. These three types of coupons are used to cross check the entire work databases and to ensure the correctness of the whole invention.

Contrary to the conventional stress-based failure criterion, a major goal of this invention was to develop a resultant force-based spot weld failure criterion with the general form of:

$$\left[\frac{f_s}{F_s}\right]^\alpha + \left[\frac{m_b}{M_b}\right]^\beta + \left[\frac{f_n}{F_n}\right]^\gamma + \left[\frac{m_t}{M_t}\right]^\mu = 1$$

in which all the denominators are the spot weld strengths obtained from the second step and the numerators are the current applied resultant loadings corresponding to each failure mode. The exponential power $\alpha$, $\beta$, $\gamma$, and $\mu$ can be determined through the following combination mode tests:

1. Combined tensile/shear and in-plane rotation test (Offset Test);
2. Combined tensile/shear and coach peel test (Inclined Peel Test);
3. Combined tensile/shear and normal pull test (Butterfly Test).

1. Combination Offset Test

Figure 25:
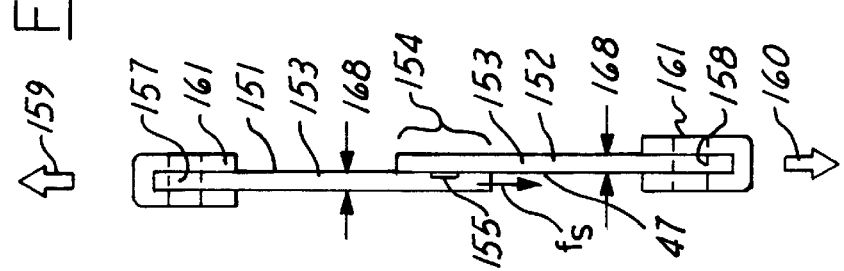
FIGS. 24–25 are, respectively, planar and side elevational views of a combination test coupon for generating shear and in-plane rotation.
Figure 24:
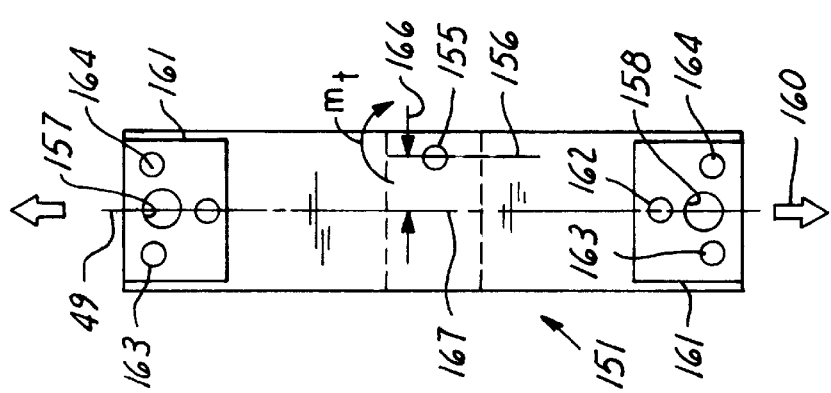

FIGS. 24 and 25 illustrate a test coupon 150 for generating the combination effect of shear and in-plane torsional rotation. The coupon 150 has a first part 151 and a second part 152, each being comprised of a strip of sheet metal 153 of the same or different selected test thickness 168; the strips 153 are overlapped at a region 154 and spot welded at a location 155 on the centerline 156 extending between two pin receiving holes 157, 158 through which machine pulling forces 159, 160 can be applied as indicated by the large arrows. To avoid any distortion due to local sheet metal rupture at the pin receiving openings 157, 158 prior to spot weld failure, another ply of sheet metal 161 is wrapped about the end of the part possessing an opening 157 or 158; the extra ply of sheet metal 161 is spot welded at locations 162, 163, 164 for reinforcement, but which spot welds do not affect the test. Such reinforcing ply ensures that the load and displacement data from the test will be accurate with respect only to the test spot weld at location 155. Upon progressive and increasing pulling forces by the test machine, both a shear force $f_s$ along the plane 165 of the overlapped strips containing the spot weld as well as a torsional in-plane rotational force $f_t$ on the spot weld will take place. The torsional moment is determined by the offset distance 166 from the centerline 167 of pull.

Since this test contains only the tensile/shear mode and the in-plane rotation mode, the general form of spot weld failure (equation a) can be reduced to:

$$\left[\frac{f_s}{F_s}\right]^\alpha + \left[\frac{m_t}{M_t}\right]^\mu = 1$$

where the tensile/shear force $f_s$ is the machine pulling force f ($f_s$=f) and the in-plane rotational torque $m_t$ is the product of the machine pulling force f and the offset 166 amount d ($m_t$=f·d). After performing this test with different offset values, the exponential powers $\alpha$, $\mu$ can be solved numerically.

2. Combination Inclined Peel Test

Figure 27:
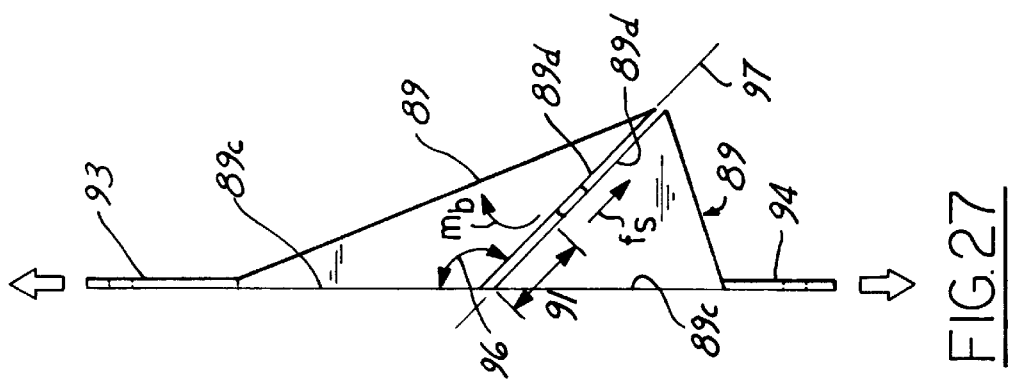
FIGS. 26–28 are, respectively, planar, side elevational and end views of a combination coupon for generating tensile shear and bending moment.
Figures 26, 28:
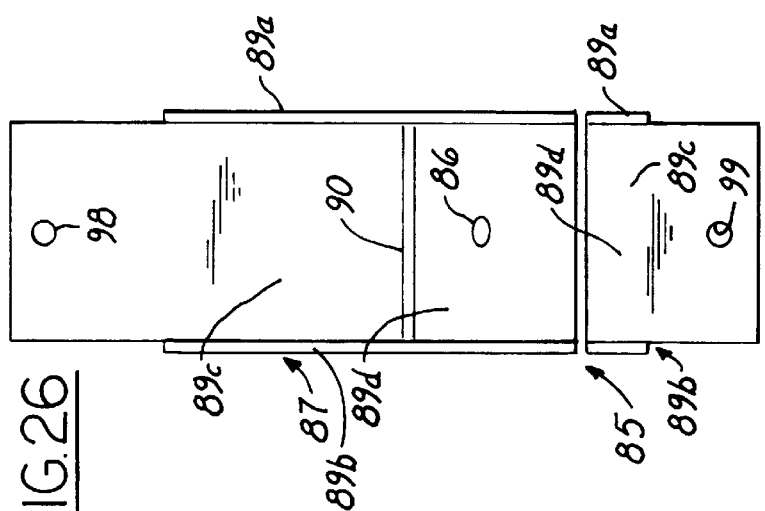

As shown in FIGS. 26–28, a test coupon 85 is designed to obtain load and displacement data for a spot weld 86 subjected to both tensile shear $f_s$ and bending moment $m_b$ (coach peel). To this end, the first and second parts 87, 88 are each constructed with a wedge-shaped box 89 having four sides 89a, 89b, 89c and 89d meeting at a line 90 to close the wedge-shaped box. Complementary shaped sides 89d of the mating boxes of the parts are welded at a single spot weld 86 centered in such sides 89d. Ears 93–94 extend from each wedged box 89 along a common plane 97 that is at an angle 96 that must be other than 90° with respect to the plane 97 of the weld. When the opposed pulling forces of the machine are applied through the pin receiving openings 98, 99 in the ears, the spot weld 86 will be subjected to a force component $f_b$ exerting a bending moment and a force component $f_s$ exerting a tensile shear force.

This test contains only the coach peel failure mode and the tensile/shear mode, the general form of spot weld failure formula (equation a) can be reduced to:

$$\left[\frac{f_s}{F_s}\right]^\alpha + \left[\frac{m_b}{M_b}\right]^\beta = 1$$

in which the tensile/shear force $f_s$ is the component of the pulling force f on the wedge boxes contact surface 97 ($f_x$=f·cos($\pi-\theta$)) and the bending moment $m_b$ is the product of the component of the pulling force f perpendicular to the surface 97 and the distance d between the front edge of the spot weld to the wedge boxes contact line 90 ($m_b$=d·sin($\pi-\theta$)). After repeating this test with different inclined angles $\theta$, the exponential power $\alpha$, $\beta$ can be solved numerically.

3. Combination Butterfly Test

Test coupon 73, shown in FIGS. 29 and 30, is designed to obtain load and displacement data for a spot weld subjected to a combination of normal pull $f_n$ and in-plane shear force $f_s$. First and second parts 74, 75 are each constructed with a shallow pan-like box structure 76 (four sides closed at one end by panel 71). Each coupon part is formed by folding a single ply of sheet metal at 77 and bending the folded leafs 78, 79 to form the shallow box structure 76 which are seam welded at its edges 72. Pin receiving holes 78, 79 are placed at corner regions 80, 81 of the parts. When the machine exerts opposed pulling forces, along line 82, on the parts, the spot weld 83 joining the mated end panels 71 of the box structure 76, which is also located on the load path, receives not only a traditionally known in-plane force $f_s$ which is parallel to the spot weld but also a normal pull force $f_n$ which is normal to the spot weld. The ratio between the shear force $f_s$ and the normal force $f_n$ is controlled by the angle 84 between the load path line 82 and the panel back surface 71.

This test contains the normal pull mode and the tensile/shear mode, wherein the general form of spot weld failure (equation a) can be reduced to:

$$\left[\frac{f_s}{F_s}\right]^\alpha + \left[\frac{f_n}{F_n}\right]^\gamma = 1$$

in which the tensile/shear force $f_s$ is the component of the pulling force f on the pan boxes contact surface 71 ($f_s$=f·cos θ) and the normal pull $f_n$ is the component of the puling force f perpendicular to the contact surface 71 ($f_n$=f·sin θ). After repeating this test with different inclined angles θ, the exponential powers α, γ can be solved numerically.

Once all the parameters α, β, γ, μ and the databases $F_s$, $F_n$, $M_b$, $M_t$ are determined, the proposed spot weld cumulative damage law (equation a) can be used for any multiaxially loaded spot weld failure evaluation. To this end, a FORTRAN program called "hmd.f" is written for automotive body structure (FIG. 1) spot weld evaluation. This program contains the spot weld cumulative damage law (equation a), its associated parameters α, β, γ, μ and the databases $F_s$, $F_n$, $M_b$, $M_t$, for different sheet metal thickness combinations from 0.65 mm to 2.45 mm. Under any given driving conditions, the spot weld applied loads $f_s$, $f_n$, $m_b$, $m_t$ (FIG. 2) can be calculated by computer modeling technique for a well modeled automotive body structure (FIG. 1). Whenever the sum of the ratios of the applied loads $f_s$, $f_n$, $m_b$, $m_t$ to its corresponding strengths $F_s$, $F_n$, $M_b$, $M_t$ is equal to or greater than 1, then the spot weld is judged to be failed. Otherwise, the spot weld is judged not to be failed.

Complete the Spot Weld Failure Criterion with Combined Mode Tests

The last step of this invention is to complete the resultant force-based spot weld failure criterion through the combined mode tests. The spot weld failure criterion proposed above is general enough to cover all possible modes of spot weld failures. By means of semi-empirical approach, its parameters α, β, γ, μ can be determined experimentally.

While the invention has been shown and described in its preferred embodiments, it will be clear to those skilled in the arts to which it pertains that many changes and modifications may be made thereto without departing from the scope of the invention.

What is claimed is:

1. A method of analyzing spot welded sheet metal structures subjected to forces that promote one or more basic failure modes of either shear tension, in-plane rotation, coach peel, normal tension, or any combination of such basic modes, the method comprising the steps of:
   (a) providing spot-welded sheet metal test coupons for analysis of the selected failure mode for the structure to be analyzed and subjecting such test coupons to progressively increasing forces that eventually achieve failure in the selected failure mode to thereby generate measured load and displacement test data;
   (b) analyzing such test data from the non-combined failure mode coupons to derive and extract spot weld strength and stiffness information;
   (c) establishing a computer math model for simulating each spot welded failure mode of the structure and populating the database thereinto to enable simulated physical tests of the structure;
   (d) creating a cumulative-damage failure criterion for the spot welded structure that ratios (i) resultant strength from the populated math model for selected combinations of load and selected combinations of time and structure thickness with (ii) strength information derived from the measured test data; and
   (e) solving such criterion by use of such resultant strength information to determine whether the criterion indicates failure for the combination of resultant strength and other values selected.

2. The method of claim 1, in which in step (e) the selected combination loadings for the test coupons to generate resultant strength information are: shear and in-plane torsional rotation, tensile shear and bending moment, and normal pull and in-plane shear.

3. The method as in claim 1, in which in step (b) strength and stiffness data is extracted from curves plotting loading as a function of displacement from the test data by use of curve fitting.

4. The method as in claim 3, in which curve fitting is solid modeling of said plotted curves on a function of varying sheet metal thicknesses for the spot welded structures.

5. The method as in claim 1, in which in step (b) the surface fitted test data is presented in a computer database for integration into said computer math models.

6. The method as in claim 1, in which in step (b) the surface fitted test data is presented in a computer data base for integration into said computer math models.

7. the method as in claim 1, in which said criterion comprises $$\left[\frac{f_s}{F_s}\right]^\alpha + \left[\frac{m_b}{M_b}\right]^\beta + \left[\frac{f_n}{F_n}\right]^\gamma + \left[\frac{m_t}{M_t}\right]^\mu = 1$$

where the denominators represent measured force test data for shear, bending, normal pull and torque respectively, and the numerators represent simulated test data for said same modes, with the exponential powers determined from combined mode measured test data.

8. The method as in claim 7 in which said exponents are determined experimentally using semi-empirical analysis.

* * * * *